US012686850B2

(12) United States Patent
Santiñà Viana et al.

(10) Patent No.: US 12,686,850 B2
(45) Date of Patent: Jul. 21, 2026

(54) THYROID MANUFACTURING PROCESS AND SPECIFICATIONS

(71) Applicant: Bioiberica, S.A.U., Barcelona (ES)

(72) Inventors: Laia Santiñà Viana, Barcelona (ES); Pere Dalmau Castañares, Barcelona (ES); Jesús Cabañas Rojo, Barcelona (ES)

(73) Assignee: Bioiberica, S.A.U., Barcelona (ES)

( * ) Notice: Subject to any disclaimer, the term of this patent is extended or adjusted under 35 U.S.C. 154(b) by 434 days.

(21) Appl. No.: 18/196,192

(22) Filed: May 11, 2023

(65) Prior Publication Data

US 2023/0365926 A1 Nov. 16, 2023

(30) Foreign Application Priority Data

May 11, 2022 (EP) ..................................... 22382456

(51) Int. Cl.
*C12N 5/071* (2010.01)
*C12M 1/33* (2006.01)
(52) U.S. Cl.
CPC ........... *C12N 5/0617* (2013.01); *C12M 45/02* (2013.01); *C12N 2500/34* (2013.01)
(58) Field of Classification Search
CPC ....... C12N 5/0617; A61K 35/26; C12M 45/02
See application file for complete search history.

(56) References Cited

FOREIGN PATENT DOCUMENTS

| | | | |
|---|---|---|---|
| CN | 105168170 A | 12/2015 | |
| CN | 109464411 B | * 5/2021 | ........... A61K 9/2866 |

OTHER PUBLICATIONS

Iveta et al Acta Veterinaria (Beograd), vol. 61, No. 5-6, 489-503, 2011 (Year: 2011).*
Children's Hospital of Philadelphia (CHOP) (printed website page from https://www.chop.edu/treatments/thyroid-hormone-replacement-therapy#:~:text=Desiccated%20thyroid%20hormone%20replacement%2C%20or,a%20synthetic%20tablet%20of%20LT4 on Sep. 22, 2025. pp. 1-10) (Year: 2025).*
Zhou (CN 109464411 B pub date:May 4, 2021; see translation). (Year: 2021).*
Stephenson, N.R., "The Standardization of Desiccated Thyroid", Journal, Jul. 1, 1967, p. 211, vol. 67, No. 1, Annals of Internal Medicine.
Anonymous, "USP Monographs: Thyroid", Monograph, Jan. 1, 2007, Pharmacopeia.
Hennessey, James V., "Historical and Current Perspective in the Use of Thyroid Extracts for the Treatment of Hypothyroidism", Journal, Oct. 1, 2015, p. 1161-1170, vol. 21, No. 10, Endocrine Practice.
Pileggi, Vincent J. et al., "Determination of Thyroxine and Triiodothyronine in Commercial Preparations of Desiccated Thyroid and Thyroid Extract", Journal, Jul. 1, 1965, p. 949-956, vol. 25, No. 7, Journal of Clinical Endocrinology and Metabolism.
Shrestha, Rupendra T. et al., "Adverse Event Reporting in Patients Treated with Thyroid Hormone Extract", Journal, May 1, 2017, p. 566-575, vol. 23, No. 5, Endocrine Practice.
Anonymous, "Thyroid", Abstract, 1 page, USP-NF/PF.

* cited by examiner

*Primary Examiner* — Marcia S Noble
(74) *Attorney, Agent, or Firm* — Hayes Soloway PC

(57) ABSTRACT

The invention relates to a thyroid manufacturing process, and more particularly, to a novel thyroid manufacturing process which encompasses a new drying step during the thyroid extraction step and a further homogenization, which allow in a thyroid product with a controlled value of hormones, and it is essentially free of virus and bacteria.

4 Claims, 1 Drawing Sheet

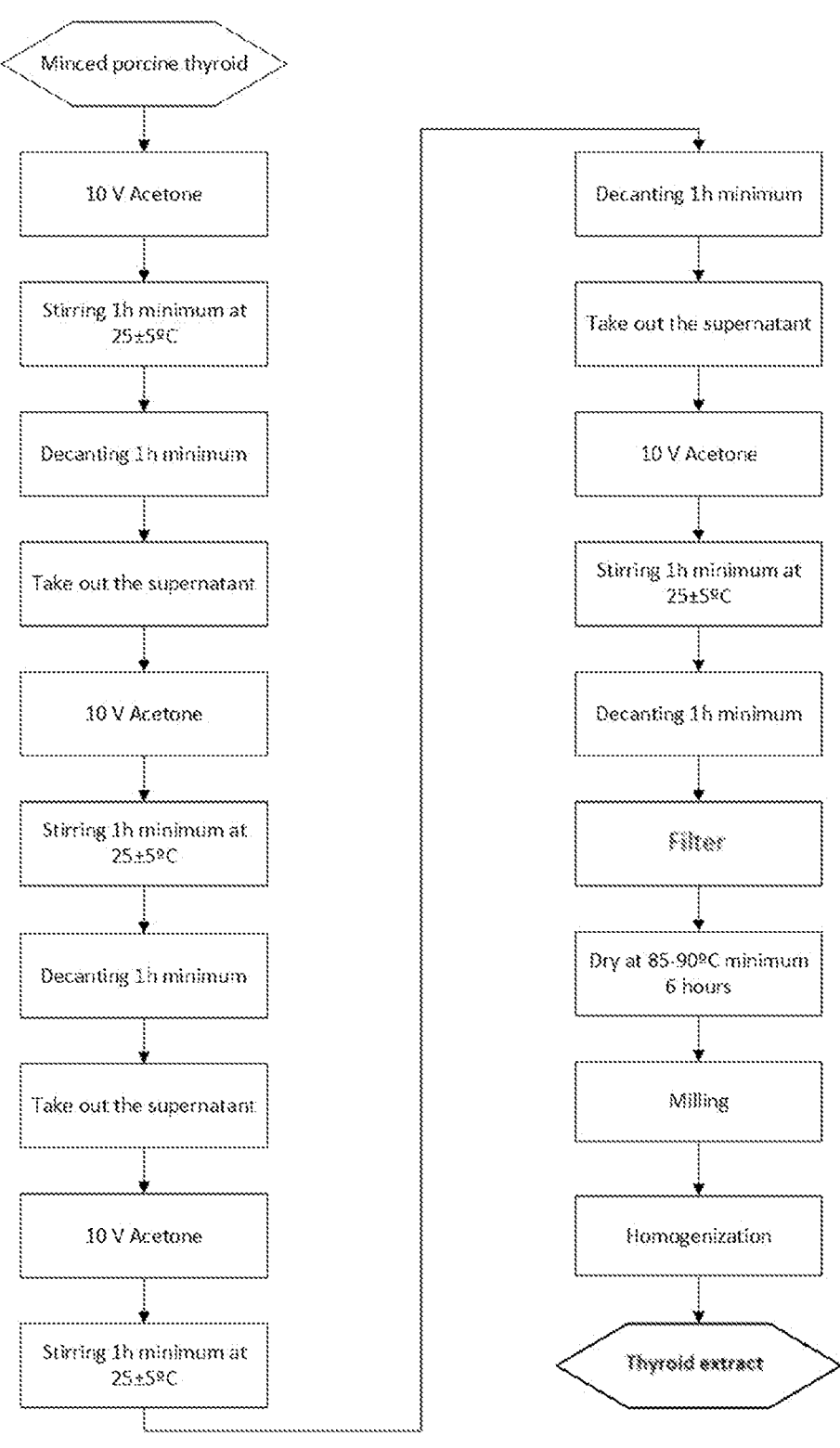

THYROID MANUFACTURING PROCESS AND SPECIFICATIONS

CROSS-REFERENCE TO RELATED APPLICATIONS AND PRIORITY

This patent application claims priority from European Patent Application No. 22382456.6 filed May 11, 2023. This patent application is herein incorporated by reference in its entirety.

BRIEF SUMMARY OF THE INVENTION

The invention relates to a thyroid manufacturing process, and more particularly, to a novel thyroid manufacturing process which encompasses a new drying step during the thyroid extraction step and a further homogenization, which allow in a thyroid product with a controlled value of hormones, and it is essentially free of virus and bacteria.

BACKGROUND ART

Thyroid replacement hormones are medications used to treat hypothyroidism, a condition in which the production of thyroid hormone in the body is abnormally low.

Thyroid hormones increase cellular metabolism (activity of cells) that is responsible for growth, development of tissues, maintenance of brain function, body temperature regulation and several other cellular processes. Low levels of thyroid hormones in the body can result in many problems given the numerous activities that they mediate.

The thyroid gland, a gland found in the lower neck is responsible for the production of thyroid hormones. It produces two main hormones, thyroxine (T4) and triiodothyronine, also known as liothyronine (T3). The hormone responsible for most of the biological effects in the body is T3. When T4 is released into the blood by the thyroid gland, most of it is converted to T3 which is responsible for the cellular metabolic processes. Commercially available thyroid hormones are either natural or synthetic (man-made). Desiccated thyroid or thyroid extract (Armor Throid, Nature-Throid), a natural thyroid hormone is derived from beef or pork. Levothyroxine sodium (for example, Synthroid, Levoxyl and Levothroid), is the synthetic version of thyroxine (T4), liothyronine sodium (Cytomel, Triostat), is the synthetic version of T3 and liotrix (Thyrolar) is a synthetic thyroid hormone containing a mixture of T4 and T3.

SUMMARY OF THE INVENTION

The present invention discloses a novel thyroid manufacturing process which encompasses a new drying step during the thyroid extraction step and a further homogenization, which allow in a thyroid product with a controlled T4/T3 value, and free of virus and bacteria.

It is important to highlight that the viral and bacterial load of the raw material in the thyroid product of the invention is reduced due to its manufacturing process, resulting in a product where these contaminants are indetectable.

A first aspect of the present invention related to a thyroid manufacturing process from porcine thyroid glands, characterized in that it comprises the following steps:
- i. Mincing of the porcine thyroid glands;
- ii. Obtention of the thyroid extract, wherein the mincing porcine thyroid glands from step i) are washed by multiple cycles in acetone, filtered and further dried at a temperature that ranges between 80° C. and 95° C., during at least 6 hours, and finally milled;
- iii. Homogenization of the milled product from step ii) with an excipient selected from lactose, maltodextrin, xylitol, lactitol, mannitol, among others, to dilute the hormones.

In a preferred embodiment, the temperature in step ii) is between 8° and 90° C., and even more preferred between 85 and 90° C.

In a preferred embodiment, the excipient in step iii) is lactose.

In another aspect, the invention relates to a thyroid product, characterised in that no virus is detected, bacteria values correspond to a total aerobic microbial count (TAMC) under $10^3$ cfu/g, the T4/T3 value is between 4.0 and 4.6, and in that is manufactured from porcine thyroid glands following the process which comprises the following steps:
- i. Mincing of the porcine thyroid glands;
- ii. Obtention of the thyroid extract, wherein the mincing porcine thyroids glands from step i) are washed by multiple cycles in acetone, filtered and further dried at a temperature that ranges between 80° C. and 95° C., during at least 6 hours, and finally milled;
- iii. Homogenization of the milled product from step ii) with lactose to dilute the hormones.

Unless otherwise defined, all technical and scientific terms used herein have the same meaning as commonly understood by one of ordinary skilled in the art to which this invention belongs. Methods and materials similar or equivalent to those described herein can be used in the practice of the present invention. Throughout the description and claims the word "comprise" and its variations are not intended to exclude other technical features, additives, components, or steps. Additional objects, advantages and features of the invention will become apparent to those skilled in the art upon examination of the description or may be learned by practice of the invention. The following examples and drawings are provided by way of illustration and are not intended to be limiting of the present invention.

DESCRIPTION OF THE DRAWINGS

FIG. 1. Scheme of the obtention of the thyroid extract (step ii)

EXAMPLES

Example 1. Thyroid Manufacturing Process from Porcine Thyroid Glands

Following the protocol disclosed in United States Pharmacopeia (2022). USP Monograph, Thyroid. USP-NF. Rockville, MD: United States Pharmacopeia, Thyroid is cleaned, dried, and powdered into thyroid gland, previously deprived of connective tissue and fat. It is obtained from domesticated animals that are used for food by humans.

On hydrolysis it yields not less than 90.0% and not more than 110.0% each of the labeled amounts of levothyroxine (T4) ($C_{15}H_{11}I_4NO_4$) and liothyronine (T3) ($C_{15}H_{12}I_3NO_4$), calculated on the dried basis. It is free from iodine in inorganic or any form of combination other than that peculiar to the thyroid gland. It may contain a suitable diluent such as lactose, sodium chloride, starch, sucrose, or dextrose.

The preparation process starts when the pig thyroid glands (100g) are chopped, and 10 volumes of acetone are added and stirred for at least 1 hour at 25° C. Then, the previous mixture is decanted for 1 hour, and the supernatant is siphoned (this process is repeated three times).

Then, the product is filtered a with paper filter with vacuum and dried with vacuum between 85 to 95° C. during at least 6 hours; the product is weighed. Subsequently, the product is placed in the mill, the product is sieved with a 500-micron sieve and the samples are sent in 20 mL vials to determine the activity T4/T3. This "final" product is then mixed with lactose to meet market requirements for Thyroid content.

Example 2. Specification for the Final Product

Appearance is performed by visual inspection of the product, describing color.

| Parameter | Limit |
|---|---|
| Appearance | Low-density, pale brown powder |
| Identification | The retention times of the peaks for liothyronine and levothyroxine of the Sample solution correspond to those of the Standard solution, as obtained in the Assay. |
| Limit of inorganic iodides | Not more than 0.01% |
| Loss on drying | Not more than 6.0% |
| Total aerobic count | Not more than $10^3$ ufc/g |
| Total yeasts and moulds count | Not more than $10^2$ ufc/g |
| E. coli | Absence/g |
| Salmonella | Absence/10 g |
| Acetone | Not more than 5000 ppm |
| Fat | Not more than 4.0% |
| Residue on ignition | Not more than 5.0% |
| Assay | |
| Liothyronine (T3, odb) | 24.3-29.7 µg/grain |
| Levothyroxine (T4, odb) | 103-125 µg/grain |
| T4/T3 ratio | 4.0-4.6 |

Identification, Limit of inorganic iodides, loss on drying, and assay of T3 and T4 are performed as described in USP Thyroid monograph. T4/T3 ratio is obtained by calculation using T4 and T3 values.

Microbiological tests (Total aerobic count, Total yeasts and moulds count, Salmonella and E. Coli) are analyzed as described in USP (61), Microbial Enumeration Tests, and USP (62), Tests for Specified Microorganisms.

Fat content is determined as described in USP Pancrelipase Monograph, Fat.

Residue on ignition is determined as described in USP (281), Residue on ignition.

Acetone is determined by Gas Chromatography with Flame Ionization Detection.

Example 3. Evaluation of the Presence of Porcine Circovirus Type 1 (Pcv-1) Infectious Viral Particles on Pk15 G6 Cells by Infectious Real-Time Qualitative PCR of Pcv-1 Spliced mRNA Sequence DNA sequence for PCV-1 were identified within the tested sample. Purpose was to determine if PCV-1 viral infectious particles were still present in the sample tested.

Tests performed in accordance with Standard Operating Procedures (SOP) TE1088 version 13, TE2041 version 10 and TE1128 version 2.

In the in vitro assay in cell culture, no infectious particles of PCV-1 were detected.

Example 4. Evaluation of the Presence of Porcine Circo Virus Type 2 (PCV-2) Infectious Viral Particles on Pk 15 Cells DNA sequence for PCV-2 were identified within the tested sample. Purpose was to determine if PCV-2 viral infectious particles were still present in the samples tested.

PCV-2 Quantitation by PCR

Positive with Ct at 33.2 12946 genomic copy/mL

PCV-2 Virus Strain Identification by Sequencinq of ORF-2 Gene

Result negative: no full genomic sequences can be obtained

PCV-2 Virus Isolation on PK15 Cells

Result negative

PCV-2 Virus Titration on PK15 Cells

Result negative

Samples Tested in triplicate were titrated in PK 15 cells for PCV2. It turned out that no detectable titre could be determined.

Meanwhile, A PCV2d isolate with the estimated titre of $10^5$ TCID50/ml was serially diluted to generate the virus dilutions with the theoretical titres of $10^4$, $10^3$, $10^2$, and 30 TCID50/ml. The viruses at these dilutions were further 10-fold serially diluted and inoculated into PK15 cells for titration (3 replicate wells per dilution). The results are shown below:

| | Theoretical titer of the PCV2d isolate at different dilutions | | | | | | | | | | | |
|---|---|---|---|---|---|---|---|---|---|---|---|---|
| | ~$10^4$ TCID50/mL | | | ~$10^3$ TCID50/mL | | | ~$10^2$ TCID50/mL | | | ~30 TCID50/mL | | |
| $10^0$ | + | + | + | + | + | + | + | + | + | + | + | + |
| $10^{-1}$ | + | + | + | + | + | + | + | + | + | + | + | + |
| $10^{-2}$ | + | + | + | + | + | + | + | + | + | − | − | − |
| $10^{-3}$ | + | + | + | + | − | − | − | − | − | − | − | − |
| $10^{-4}$ | − | + | − | − | − | − | − | − | − | − | − | − |
| $10^{-5}$ | − | − | − | − | − | − | − | − | − | − | − | − |
| $10^{-6}$ | − | − | − | − | − | − | − | − | − | − | − | − |
| $10^{-7}$ | − | − | − | − | − | − | − | − | − | − | − | − |
| | $5.58 \times 10^4$ TCID50/mL | | | $5.58 \times 10^3$ TCID50/mL | | | $3.16 \times 10^3$ TCID50/mL | | | $3.16 \times 10^2$ TCID50/mL | | |

Obtained titer of the PCV2d isolate at different dilutions

This complementary information leads to validate the PCV2 titration and isolation assays.

Example 5. Detection of Porcine and Bovine Viruses Using Yero, Bt and St Cell Lines and Real-Time Qualitative PCR Tests were performed according to 9CFR guideline and to technical document TD0981-145 #01.

For qPCR, samples analysed were tested diluted 10-fold, 100-fold and 1000-fold. For the same reason described in certificate 145/20/TD0981/03 and related deviation form FI-2020-029, only results obtained with the dilution 100-fold due to matrix properties are used to validate the assay.

The in vitro cell culture assay was performed in 13 different batches no infectious particles of the following viruses were detected: Parainfuenzae 3 virus, Bovine Parainfluenzae 3 Virus, Bovine Viral Diarrhea Virus (BVDV), Bovine AdenoVirus 3 (BAV-3), Blue Tongue Virus (BTV), Bovine Parvovirus (BPV), Reovirus 3 (Reo3), Rabies Virus, Bovine Respiratory Syncytial Virus (BRSV), Transmissible GastroEnteritis Virus (TGEV), Porcine ParvoVirus (PPV), Porcine AdenoVirus (PAV), and Porcine Hemagglutinating Encephalomyelitis Virus (PHEV).

Porcine viruses were tested since the porcine starting material. Bovine viruses were testing for the lactose from bovine origin.

The invention claimed is:

1. A thyroid manufacturing process from porcine thyroid glands, comprising the following steps:
   i. mincing of the porcine thyroid glands;
   ii. washing the minced porcine thyroid glands from step i) using multiple cycles of acetone;
   iii. filtering the washed thyroid glands of step ii);
   iv. drying the filtered thyroid glands of step iii) at a temperature that ranges between 80° C. and 95° C., for at least 6 hours;
   v. milling the dried thyroid glands of step iv) obtaining a milled thyroid product containing thyroid hormones; and
   vi. homogenizing the milled thyroid product from step v) with an excipient to dilute the concentration of the thyroid hormones.

2. The thyroid manufacturing process according to claim 1, wherein the temperature in step iv) is between 85 and 90° C.

3. The thyroid manufacturing process according to claim 1, wherein the excipient in step vi) is selected from lactose, maltodextrin, xylitol, lactitol, and mannitol.

4. The thyroid manufacturing process according to claim 3, wherein the excipient in step vi) is lactose.

* * * * *